United States Patent [19]

Andrén

[11] 4,133,562
[45] Jan. 9, 1979

[54] SEPARATION COLUMN

[75] Inventor: Lars-Göran H. Andrén, Upsala, Sweden

[73] Assignee: Pharmacia Fine Chemicals AB, Upsala, Sweden

[21] Appl. No.: 784,823

[22] Filed: Apr. 5, 1977

[51] Int. Cl.² .............................................. F16L 55/00
[52] U.S. Cl. ..................................... 285/187; 285/235
[58] Field of Search ....... 285/187, 235, 237, DIG. 10, 285/DIG. 12

[56] References Cited

U.S. PATENT DOCUMENTS

| 3,236,543 | 2/1966 | Mueller | 285/423 X |
| 3,243,211 | 3/1966 | Wetmore | 285/DIG. 10 |
| 3,423,518 | 1/1969 | Weagant | 285/381 X |
| 3,544,672 | 12/1970 | Goda et al. | 285/381 X |
| 3,957,382 | 5/1976 | Greuel et al. | 285/381 X |

Primary Examiner—Wayne L. Shedd
Attorney, Agent, or Firm—Witherspoon, Lane & Hargest

[57] ABSTRACT

A separation column comprising a column tube and terminal flanges, wherein the terminal flanges are attached to the column tube by means of a two-layer material which encloses a portion of the column tube and a portion of one of said terminal flanges, said two-layer material comprising a fusible plastic layer in contact with the column tube and said terminal flange and an outer hose of shrinking plastic, having been subjected to a heat treatment causing the fusible plastic layer to fuse and the shrinking plastic hose to shrink.

6 Claims, 1 Drawing Figure

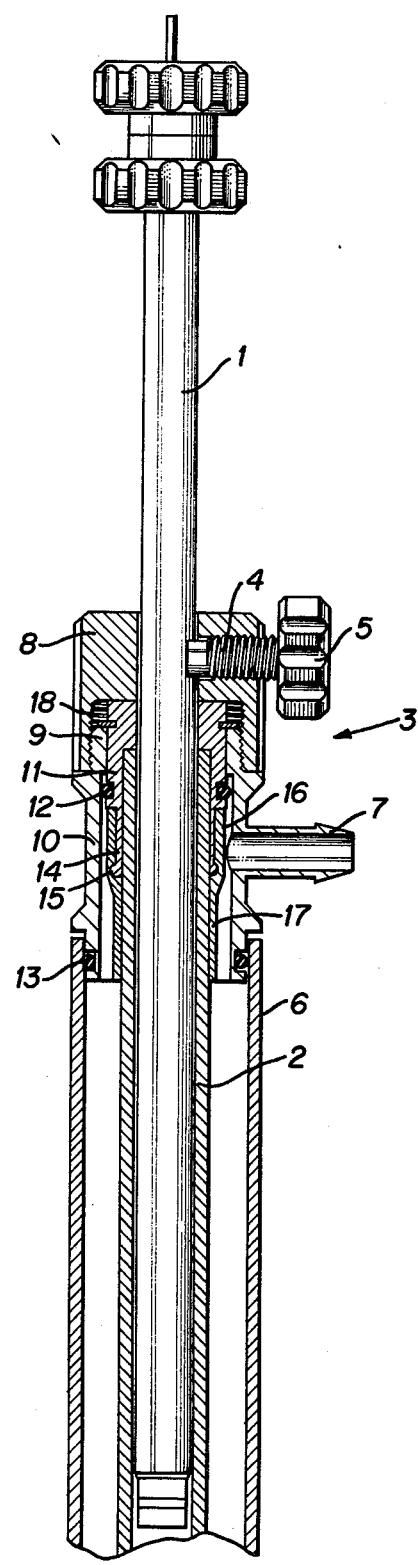

SEPARATION COLUMN

The invention refers to so called separation columns to be used preferably in laboratories, the invention also comprising a method of assembling such a column.

Separation columns comprise an inner tube, normally of glass, the so called column tube, in which the separation is performed and at the ends some kind of flanges for mounting means supplying liquids to and withdrawing them from the column tube. These flanges are also used for mounting and sealing a cooler casing, if used, around the column tube enabling temperature controlling fluids to be circulated through the interspace.

Previously used columns have been comparatively expensive and difficult to manufacture because it has been necessary to shape the column tube in a specific way with widened ends necessitating specific manufacture of glass tubes having such terminal flanges for this. It is the purpose of the present invention to eliminate this drawback by providing a column and a method of assembling such a column where specifically manufactured glass tubes are no longer required and ordinary straight standard tubes can be used.

When trying to realize this purpose by attempting to use ordinary straight standard tubes in place of the previously used special tubes having flanged ends it is, however, necessary to solve the problem securely to attach the terminal flanges at the glass tube paying consideration to the fact that the joint during use of the column is exposed to several different types of solvents. This means that most types of cement are unsuitable, in particular as the end flanges often have to be manufactured of plastic materials having unsatisfactory cementing properties.

There is the alternative possibility to provide the glass tube with threads and to attach the terminal flanges by screwing and, while this is a possible solution, it requires a complicated working of the glass tube and forbids direct use of straight standard tubes.

The above objects are realized according to the invention in a device and a method according to the preamble of the attached claims and by using the characteristic features of the invention as defined in the claims.

The enclosed drawing illustrating the inventive idea shows the upper half of a column shown in section and with certain parts shown in an elevation for the sake of clarity.

The separation column shown in the drawing has a mantle tube 6 within which a column tube 2 extends. A temperature controlling medium is caused to circulate in the interspace between the mantle tube 6 and the column tube 2, this medium being supplied and discharged respectively by means of conduits not shown and connected to nipples one of which only is shown at 7 in the drawing. Connecting nipple 7 forms a part of a terminal sleeve 10 which in its mounted position extends slightly into the mantle tube 6, a sealing ring 13 sealing the terminal sleeve in relation to the mantle tube. The upper part of the terminal sleeve 10 has an outwardly threaded portion 9 adapted to cooperate with an upper terminal piece 8 provided with corresponding inner thread. Moreover the terminal piece 8 is provided with a radially extending threaded bore through which a mounting screw 4 having a control knob 5 extends. Both the column tube 2 and the mantle tube 6 are straight glass tubes and no specifically blown glass tube constructions are required in connection with the present invention. The terminal sleeve 10 and the terminal piece 8 are made of workable plastic material and, accordingly, the threaded portions are easily manufactured.

At its end portions column tube 2 is provided with end flanges, the upper one of which is shown at 11 in the drawing. This end flange 11 is attached to the column tube 2 in a way to be described later on and comprises sealing means such as the O-ring 12 for sealing between end flange 11 and end sleeve 10 and mounting means 18, such as a locating ring, key means or the like adapted to retain the column tube 2 in proper position in the separation column. End flange 11 as well as the rest of the mounting means may advantageously be made of plastic materials which are resistive to solvents, for example a polytetrafluoroethylene material.

It will be appreciated that problems are encountered if a sleeve of such material as polytetrafluoroethylene is to be attached to a glass tube, the present invention, however, offering a solution of this problem.

In accordance with the present invention the straight column tube 2 of glass is attached to the end flange of solvent resistive, workable plastic material in the following way. The lower portion or extension 14 of the terminal flange 11 which may be terminated by a bead 15 is outwardly threaded onto an outer portion of the column tube 2. A layer of fusible plastic is applied over a portion of the extension 14 of the end flange 11 and a portion 17 of the column tube 2 consisting of glass. This layer of fusible plastic may be in the form of a fusible hose or fusible tape. A hose of shrinking plastic is outwardly applied onto said fusible plastic layer. As a rule the hose material is a polyolefine (polyethylene), polyvinylchloride (PVC) or fluoroplastics such as polyvinylidene fluoride, polytetrafluoroethylene (PTFE), fluoroethylene polymere (FEP). Shrinking plastics are manufactured by spray forming to the shape the product is to have in its shrunk condition. Thereafter the product is irradiated with high-energy electrons (beta rediation) causing cross-links to be formed between the molecule chains. Subsequently these will act as "elastic memories". When the products are heat treated immediately above the normal melting point of the plastic it will not melt but rather become resilient. When the hose simultaneously is exposed to internal overpressure the hose will be enlarged, this enlargement being retained if the overpressure is maintained during cooling. When again heated above the normal melting point the plastic will tend to resume its original shape.

In order to obtain improved sealing and better adhesion a fusible hose may be inserted into the skrinking hose. The fusible plastic layer and the shrinking plastic hose may be combined into a hose structure, the fusible hose comprising a non-irradiated polyolefine if the shrinking hose is of olefine type. It is also possible to combine a fusible hose of FEP with a shrinking hose of irradiated PTFE. When combining fusible plastic and shrinking plastic care should be taken that the fusible plastic fuses at the temperature at which the shrinking plastic shrinks. A ready-made shrinking hose of irradiated polyolefine combined with an internal fusing layer of non-irradiated polyolefine is available on the market. It is also possible to buy shrinking hose of PTFE enclosing an untreated inner hose of FEP. When the combination hose or fusible plastic layer and shrinking plastic hose have been applied and heat treated at a temperature immediately above the fusing and shrinking temperatures the fusing layer will fuse and adheres to the base while the shrinking hose will shrink and perform a radially directed force against the fusible layer while simultaneously absorbing axially directed forces between the terminal flange and the column tube. It has been experimentally shown that the joint has no tendency towards fatigue after extended use.

The assembly of the column according to the invention is performed in the following way. The terminal flange 11 is provided with the two-layer hose as at 16, said hose comprising said fusible plastic layer and said shrinking plastic hose. The unit so formed is threaded onto the column tube 2 in the correct position as indicated at 17. By the application of heat the fusible plastic layer is caused to fuse and the shrinking plastic hose is caused to contract so that an absolutely safe and solid joint is obtained. The column tube 2 provided in this way with the terminal flange is thereafter assembled with the terminal sleeve 10 and is held in place by the locking ring 18. Subsequently the unit is combined with the mantle tube 6. Thereafter the upper terminal piece 8 is screwed-on, the flow adaptor 1 is inserted and the mounting screw 4 is so tightened that it comes into contact with the flow adapter. Thereafter the separation column is ready for use.

According to the invention there is obtained a column manufactured of straight tubes only, thus eliminating the expensive manufacture of special glass required in prior-art construction. An absolutely safe assembly is obtained which resists any stresses incident to the filling and use of the column. By using workable, easily manufactured and cheap plastic components the construction is rendered cheaper and the assembly is essentially facilitated in relation to priorart devices.

The expert of the field will appreciate that variations and modifications may be made within the frame of the invention such as defined in the present claims without departure from the basic idea of the invention. Certain presently preferred materials have been mentioned above, it being obvious that other types of material having similar properties may be used provided they yield the same function as described above.

What we claim is:

1. A separation column comprising a column tube and terminal flanges, said terminal flanges being sealed relative to the column tube by means of a two-layer material which encloses a portion of the column tube and a portion of one of said terminal flanges, said two-layer material comprising an inner fusible plastic tubular layer in contact with the column tube and said terminal flange and a concentric outer tubular layer of shrinking plastic, having been subjected to a heat treatment causing the fusible plastic layer to fuse and adhere to said terminal flange and column tube, and the shrinking plastic hose to shrink and exert a radially directed force against said fusible layer.

2. The apparatus of claim 1 wherein said separation column includes a mantle tube, and said column tube is positioned internal of and concentric with said mantle tube and is spaced therefrom and sealed with respect thereto by means of said flanges.

3. The apparatus of claim 2 wherein the surface of said one terminal flange in contact with said inner fusible plastic tubular layer includes a beaded portion about which said fusible plastic is fused and adhered.

4. The apparatus of claim 3 wherein said terminal flanges comprise a terminal sleeve positioned internal of and concentric with said mantle tube and in sealing engagement therewith, and said one terminal flange extends into said terminal sleeve in sealing engagement therewith.

5. The apparatus of claim 4 wherein said separation column includes an upper terminal piece attached to said terminal sleeve and having an axially extending bore, and a flow adapter extending through said bore into said column tube.

6. The apparatus of claim 5 wherein said terminal piece includes a radially extending threaded bore through which a mounting screw having a control knob extends for controlling said flow adapter.

* * * * *

UNITED STATES PATENT AND TRADEMARK OFFICE
CERTIFICATE OF CORRECTION

PATENT NO. : 4,133,562
DATED : January 9, 1979
INVENTOR(S) : Lars-Göran Hjalmar Andren It is certified that error appears in the above-identified patent and that said Letters Patent are hereby corrected as shown below:

On the cover page the following should be added

-- [30] Foreign Application Priority Data

Apr. 14, 1976        Sweden ...........7604445 --.

Signed and Sealed this

Nineteenth Day of June 1979

[SEAL]

Attest:

RUTH C. MASON
*Attesting Officer*

DONALD W. BANNER
*Commissioner of Patents and Trademarks*